United States Patent [19]

Benés et al.

[11] Patent Number: 5,753,646
[45] Date of Patent: May 19, 1998

[54] SUBSTITUTED DIHYDRODIBENZO/B,F/ AZEPINES, METHOD OF THEIR PREPARATION, THEIR USE IN THE TREATMENT OF SOME CENTRAL NERVOUS SYSTEM DISORDERS, AND PHARMACEUTICAL COMPOSITIONS CONTAINING THEM

[75] Inventors: Jan Benés; Patricio M. V. A. Soares Da Silva, both of Oporto, Portugal

[73] Assignee: Portela & Ca., S.A., Oporto, Portugal

[21] Appl. No.: 673,819

[22] Filed: Jun. 27, 1996

[30] Foreign Application Priority Data

Jun. 30, 1995 [PT] Portugal ..................... 101732

[51] Int. Cl.$^6$ ................. C07D 223/18; A61K 31/55
[52] U.S. Cl. ........................... 514/217; 540/589
[58] Field of Search ..................... 540/589; 514/217

[56] References Cited

U.S. PATENT DOCUMENTS 5,466,683  11/1995  Sterling et al. .................. 514/80

FOREIGN PATENT DOCUMENTS

| 747086 | 3/1970 | Belgium . |
| 892882 | 10/1982 | Belgium . |
| 0028028 | 5/1981 | European Pat. Off. . |
| 2011087 | 9/1970 | Germany . |
| 2011045 | 10/1970 | Germany . |
| 218889 | 2/1985 | Germany . |
| 1310120 | 3/1973 | United Kingdom . |
| 1310571 | 3/1973 | United Kingdom . |

OTHER PUBLICATIONS

*Drug Evaluation*, vol. 43, No. 6., pp. 873-888, S. M. Grant and Diana Faulds, "Oxcarbazepine—A Review of its Pharmacology and Therapeutic Potential in Epilepsy, Trigeminal Neuralgia and Affective Disorders", 1992.

A. Korolkovas, *Essentials of Medicinal Chemistry*, 1988, John Wilson & Sons, New York, pp. 101–106.

R.C. Larock, *Comprehensive Organic Transformations*, 1989, VCH Publishers, pp. 966–972.

Primary Examiner—Mukund J. Shah
Assistant Examiner—Bruck Kifle
Attorney, Agent, or Firm—Ostrolenk, Faber, Gerb & Soffen, LLP

[57] ABSTRACT

New compounds of general formula I, including all possible stereoisomers, are described

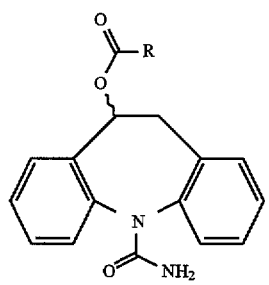

wherein:

R is hydrogen, alkyl, aminoalkyl, halogenalkyl, aralkyl, cycloalkyl, cycloalkylalkyl, alkoxy, phenyl or substituted phenyl or pyridyl group.

A process for their preparation consists of reaction of compound II

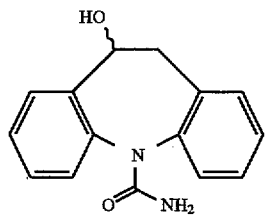

with an acylating agent.

10 Claims, No Drawings

SUBSTITUTED DIHYDRODIBENZO/B,F/ AZEPINES, METHOD OF THEIR PREPARATION, THEIR USE IN THE TREATMENT OF SOME CENTRAL NERVOUS SYSTEM DISORDERS, AND PHARMACEUTICAL COMPOSITIONS CONTAINING THEM

The present invention relates to substituted dihydrodibenz/b,f/azepines, to the method of their preparation and to pharmaceutical compositions containing them. The compounds have valuable pharmaceutical properties in the treatment of some central and peripheric nervous system disorders.

Compounds with the dibenz/b,f/azepine ring system are well known and some of them have been used widely for treatment of some pathological states in humans. For example dibenz/b,f/azepine-5-carboxamide (carbamazepine) has become established as an effective agent in the management of epilepsy, trigeminal neuralgia and affective disorders. However, its administration in humans is complicated by its potent induction of hepatic oxidative enzymes, by adverse central nervous system effects, and frequent and serious idiosyncratic reactions. An analogue of carbamazepine, 10,11-dihydro-10-oxo-5H-dibenz/b,f/azepine-5-carboxamide (oxcarbazepine, see e.g. German Patent 2.011.087) circumvents the problem of induction of hepatic microsomal enzymes by virtue of its differing metabolic profile, while problems remain with others mentioned above. It was proved that oxcarbazepine is metabolised in mammals to 10,11-dihydro-10-hydroxy-5H-dibenz/b,f/azepine-5-carboxamide which exhibits comparable antiepileptic activity to the parent drug. Use of this metabolite as an antiepileptic drug was described (see e.g. Belgian Patent 747.086), but it is not used in practice, because its preferred oral administration is hampered by its low bioavailability.

The invention aims to achieve an improvement in some of the above mentioned characteristics and relates to new compounds of general formula I, including all possible stereoisomers

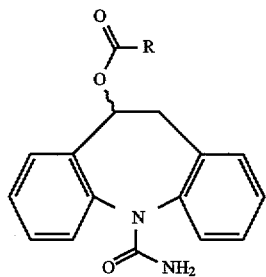

wherein:
R is hydrogen, alkyl, aminoalkyl, halogenalkyl, aralkyl, cycloalkyl, cycloalkylalkyl, alkoxy, phenyl or substituted phenyl or pyridyl group; the term alkyl means carbon chain, straight or branched, containing from 1 to 18 carbon atoms; the term halogen represents fluorine, chlorine, bromine or iodine; the term cyctoalkyl represents a saturated alicyclic group with 3 to 6 carbon atoms; the term aryl represents unsubstituted phenyl group or phenyl substituted by alkoxy, halogen or nitro group.

Preferred compounds of formula I include:
1. 10-acetoxy-10,11-dihydro-5H-dibenz/b,f/azepine-5-carboxamide
2. 10-benzoyloxy-10,11-dihydro-5H-dibenz/b,f/azepine-5-carboxamide
3. 10-(4-methoxybenzoyloxy)-10,11-dihydro-5H-dibenz/b,f/azepine-5-carboxamide
4. 10-(3-methoxybenzoyloxy)-10,11-dihydro-5H-dibenz/b,f/azepine-5-carboxamide
5. 10-(2-methoxybenzoyloxy)-10,11-dihydro-5H-dibenz/b,f/azepine-5-carboxamide
6. 10-(4-nitrobenzoyloxy)-10,11-dihydro-5H-dibenz/b,f/azepine-5-carboxamide
7. 10-(3-nitrobenzoyloxy)-10,11-dihydro-5H-dibenz/b,f/azepine-5-carboxamide
8. 10-(2-nitrobenzoyloxy)-10,11-dihydro-5H-dibenz/b,f/azepine-5-carboxamide
9. 10-(4-chlorobenzoyloxy)-10,11-dihydro-5H-dibenz/b,f/azepine-5-carboxamide
10. 10-(3-chlorobenzoyloxy)-10,11-dihydro-5H-dibenz/b,f/azepine-5-carboxamide
11. 10-(2-acetoxybenzoyloxy)-10,11-dihydro-5H-dibenz/b,f/azepine-5-carboxamide
12. 10-propionyloxy-10,11-dihydro-5H-dibenz/b,f/azepine-5-carboxamide
13. 10-butyryloxy-10,11-dihydro-5H-dibenz/b,f/azepine-5-carboxamide
14. 10-pivaloyloxy-10,11-dihydro-5H-dibenz/b,f/azepine-5-carboxamide
15. 10-[(2-propyl)pentanoyloxyl]-10,11-dihydro-5H-dibenz/b,f/azepine-5-carboxamide
16. 10-[(2-ethyl)hexanoyloxy]-10,11-dihydro-5H-dibenz/b,f/azepine-5-carboxamide
17. 10-stearoyloxy-10,11-dihydro-5H-dibenz/b,f/azepine5-carboxamide
18. 10-cyclopentanoyloxy-10,11-dihydro-5H-dibenz/b,f/azepine-5-carboxamide
19. 10-cyclohexanoyloxy-10,11-dihydro-5H-dibenz/b,f/azepine-5-carboxamide
20. 10-phenylacetoxy-10,11-dihydro-5H-dibenz/b,f/azepine-5-carboxamide
21. 10-(4-methoxyphenyl)acetoxy-10,11-dihydro-5H-dibenz/b,f/-azepine-5-carboxamide
22. 10-(3-methoxyphenyl)acetoxy-10,11-dihydro-5H-dibenz/b,f/-azepine-5-carboxamide
23. 10-(4-nitrophenyl)acetoxy-10,11-dihydro-5H-dibenz/b,f/azepine-5-carboxamide
24. 10-(3-nitrophenyl)acetoxy-10,11-dihydro-5H-dibenz/b,f/azepine-5-carboxamide
25. 10-nicotinoyloxy-10,11-dihydro-5H-dibenz/b,f/azepine-5-carboxamide
26. 10-isonicotinoyloxy-10,11-dihydro-5H-dibenz/b,f/azepine-5-carboxamide
27. 10-(4aminobutanoyloxy)-10,11-dihydro-5H-dibenz/b,f/azepine-5-carboxamide
28. 10-(2-amino-3-methylbutanoyloxy)-10,11-dihydro-5H-dibenz/b,f/-azepine-5-carboxamide
29. 10-chloroacetoxy-10,11-dihydro-5H-dibenz/b,f/azepine-5-carboxamide
30. 10-bromoacetoxy-10,11-dihydro-5H-dibenz/b,f/azepine-5-carboxamide
31. 10-formyloxy-10,11-dihydro-5H-dibenz/b,f/azepine-5-carboxamide
32. 10-ethoxycarbonyloxy-10,11-dihydro-5H-dibenz/b,f/azepine-5-carboxamide
33. 10-(2-chloronpropionyloxy)-10,11-dihydro-5H-dibenz/b,f/azepine-5-carboxamide Another aspect of the invention comprises the method of useful preparation of compounds of formula I where substituent R is defined above, by reacting the compound of formula II

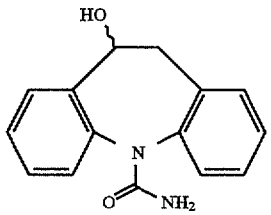

with a compound of the general formula III

A—CO—R    III wherein:

R is the same as defined above for general formula I;

A is hydroxy, halo or —O—CO—R group or —O—CO—OR' group, wherein R' is lower alkyl ($C_1$-$C_4$), in the presence of condensing agents which include dicyclohexylcarbodiimide, carbonyldiimidazole and ethyl- or isobutylchloroformate and/or in the presence of organic or inorganic bases such as pyridine, triethylamine, quinotine, imidazole or alkyl carbonates, in inert solvents such as hydrocarbons (e.g. hexane, cyclohexane), ethers (e.g. diethylether, tetrahydrofurane), chlorinated alkanes (e.g. dichloromethane, 1,2-dichloroethane) or aprotic dipolar solvents (e.g. acetonitrile, dimethylformamide) or the reaction can be run in a mixture of the the above mentioned solvents or in the absence of any solvent.

The acylation reaction described above may be performed at various temperatures and pressures, e.g. between 0° C. and boiling temperature of the reaction mixture and at atmospheric or elevated pressure.

Compound of the formula II is known (see e.g. German Patent 2.011.045), and compounds of the formula III are also well known and can be made by the methods known to those skilled in the art, including e.g. methods described in the book "Comprehensive Organic Transformations" by Richard C. Larock, VCH Publishers, 1989, pp 966 to 972. In the processes described above, it is sometimes necessary to protect certain functional groups during the reactions. Conventional protecting groups such as benzyloxycarbonyl- or tertbutyloxycarbonyl- are operable and can be removed after acylation by standard procedures.

Still another aspect of the invention comprises a method of making a pharmaceutical composition comprising of mixing a compound of formula I with a pharmaceutically acceptable carrier.

Compounds of formula I have valuable pharmaceutical properties in the treatment of some central and peripheric nervous system disorders, namely in treatment of epilepsy, trigeminal neuralgia, affective brain disorders and nervous function changes in degenerative and post-ischemic diseases.

Epilepsy is one of the most common afflictions of man with a prevalence of approximately 1%. Since the time of Hughlings Jakson more than 100 years ago, epileptic seizures have been known to represent "occasional, sudden, excessive, rapid and local discharges of nerve tissue". Epileptic seizures are divided fundamentally into two groups: partial and generalised. Partial seizures are those in which the discharge begins locally, and often remains localised. Generalised seizures involve the whole brain, including the reticular system, thus producing abnormal electrical activity throughout both hemispheres and immediate loss of consciousness. Partial seizures are divided in (a) partial simple seizures, (b) complex partial seizures and (c) partial seizures secondarily generalised. The generalised seizures include: (1) tonic-clonic seizures (grand mat), (2) absence seizures (petit mal), (3) myoclonic seizures, (4) atonic seizures, (5) clonic seizures and (6) tonic seizures. Epilepsy, in contradistinction to seizures, is a chronic disorder characterised by recurrent seizures (Gastaut, H.: Dictionary of epilepsy. World Health Organization, Geneve, 1973).

There are two ways in which drugs might abolish or attenuate seizures: (a) through effects on altered neurones of seizure foci to prevent or reduce their excessive discharge, and (b) through effects that would reduce the spread of excitation from seizure foci and prevent disruption of function of normal aggregates of neurones. The majority, if not all, of the available antiepileptic drugs work at least by the second mechanism, since all modify the ability of the brain to respond to various seizure-evoking stimuli. Convulsant drugs, such as pentylenetetrazol (metrazol) are often used, particularly in the testing of anticonvulsant agents, and seizures caused by electrical stimulation of the whole brain are used for the same purpose. It has been found empirically that activity in inhibiting metrazol-induced seizures and in raising the threshold for production of electrically induced seizures is a fairly good index of effectiveness against absence seizures. On the other hand, activity in reducing the duration and spread of electrically induced convulsions correlates with effectiveness in controlling other types of epilepsy, such as tonic-clonic seizures.

The anticonvulsant effect of compounds of formulae I was studied in a model of electrically induced convulsions, the maximal electroshock (MES) test, and in a model of chemical induced convulsions, the metrazol test. The MES test allows the evaluation of the ability of drugs to prevent electrically induced tonic hindlimb extension in rats, the efficacy of which is thought to be predictive of anticonvulsant efficacy against generalised tonic-clonic seizures in man (grand mal). The metrazol test predicts the ability of potential antiepileptic agents to prevent clonic seizures and to be effective against absence seizures (petit mal).

MATERIALS AND METHODS

Male Wistar rats obtained from the animal house of the Instituto Gulbenkian de Ciência (Oeiras, Portugal) and weighing 180 to 280 g were used. Animals were kept two per cage under controlled environmental conditions (12 hr light/dark cycle and room temperature 24° C.). Food and tap water were allowed ad libitum and the experiments were all carried out during daylight hours.

1—MES test

MES stimulation was applied for 0.2 s, using a Ugo Basile ECT unit 7801, with a frequency of 100 Hz, pulse width of 0.6 ms and a current of 150 mA through bipolar corneal electrodes. A drop of electrolyteianaesthetic, oxibuprocaine chloride, was applied in the eyes of all animals immediately before placement of corneal electrodes. Abolition of the hindleg tonic extensor component, was used as the endpoint. These experimental conditions produced tonic-clonic convulsions in 97% of animals tested and only rats showing typical tonic-lonic convulsions were used. All rats were submitted to a maximum of 3 MES sessions: the first MES session was performed to screen the animals and select those rats presenting a typical convulsive behaviour. The day after, rats were given the compounds to be tested or the vehicle and submitted to a second MES session 2 or 4 hours after the administration of test drugs. The third MES session was performed at 6, 8 or 12 hours after the administration of test drugs. The time interval between each MES session was at least 4 hours (rats tested at 2 hours were retested at 6 hours and rats tested at 4 hours were retested at 8 hours). The evaluation of the anticonvulsive profile of test drugs was based on the duration of the tonic phase (in seconds) being each rat its own control (internal control) as obtained in the first MES session. An external control group was also studied; in this particular case, rats were given the vehicle and submitted to the three MES sessions procedure, as described above. All drugs used were suspended in 0.5% carboxymethylcellulose (4 ml/kg) and given by stomach tube.

2—Metrazol test

Administration of compounds of formula I was performed 2 hours before the administration of metrazol. Metrazol (75 mg/kg) was given subcutaneously in the back; this dose of metrazol was found to produce convulsions in 95% of the animals. The parameters observed concern the duration of seizures in a 30 minute observation period following the administration of metrazol. $ED_{50}$(mg/kg) is the dose giving 50% reduction of duration of the seisure.

Results

1—MES test

At the highest dose tested (35 mg/kg), compounds of formula I produced a complete protection against MES after 2 hours of administration. At 4 and 8 hours the protection conferred by compounds of formula I was similar to that produced by the reference compound carbamazepine. At the highest dose tested (35 mg/kg), carbamazepine produced a complete protection against MES after 2 hours of administration; at 4 and 8 hours after administration the protection conferred was still above 80%. The $ED_{50}$ values for carbamazepine at 2, 4 and 8 hours after the administration was 7.95, 15.80 and 2.70 mg/kg, respectively. In contrast to oxcarbazepine and similarly to carbamazepine compounds of formula I were found to be more potent after 8 hours with a $ED_{50}$ value substantially lower than that for oxcarbazepine. The $ED_{50}$ values for compounds of formula I at 2, 4 and 8 hours after the administration was 17.97, 13.90 and 3.90 mg/kg, respectively. Oxcarbazepine performed not so potently as did carbamazepine and compounds of formula I. The $ED_{50}$ values for oxcarbazepine at 2, 4 and 8 hours after the administration was 16.18, 16.28 and 13.24 mg/kg, respectively.

2—Metrazol test

Compounds of formula I were effective in protecting rats against convulsions induced by metrazol. The highest effective dose of compounds of formula I was 30 mg/kg and reduced the total seizure time by 69%. The $ED_{60}$ value for compounds of formula I was 14.7 mg/kg. Carbamazepine at 30 and 60 mg/kg produced a 41% and 44%, respectively, decrease in total seizure time. Oxcarbazepine performed less potently than did carbamazepine. At 30 and 60 mg/kg oxcarbazepine a 3% and 32% decrease in total seizure time was observed, respectively.

CONCLUSION

Compounds of formula I possess valuable antiepileptic activity as screened in the MES and metrazol tests and are endowed with greater or similar anticonvulsant potency to that of reference compounds carbamazepine or oxcarbazepine.

The utilisation of compounds of formula I may prove useful in man for the treatment of some other central and peripheric nervous system disorders, e.g. for trigeminal neuralgia and brain affective disorders nervous function alterations in degenerative and post-ischemic diseases.

For the preparation of pharmaceutical compositions from the compounds of formula I, inert pharmaceutically acceptable carriers are admixed with the active compounds. The pharmaceutically acceptable carriers may be either solid or liquid. Solid form preparations include powders, tablets, dispersible granules and capsules. A solid carrier can be one or more substances which may also act as diluents, flavoring agents, solubilizers, lubricants, suspending agents, binders or tablet disintegrating agents; it may also be an encapsulating material.

Preferably, the pharmaceutical preparation is in unit dosage form, e.g. packaged preparation, the package containing discrete quantities of preparation such as packeted tablets, capsules and powders in vials or ampules.

The dosages may be varied depending on the requirement of the patient, the severity of the disease and the particular compound being employed. For convenience, the total daily dosage may be divided and administered in portions throughout the day. Determination of the proper dosage for a particular situation is within the skill of those in the medical art.

The invention disclosed herein is exemplified by the following examples of preparation, which should not be construed to limit the scope of the disclosure. Alternative pathways and analogous structures may be apparent to those skilled in the art.

EXAMPLES

Example 1

10-formyloxy-10,11-dihydro-5H-dibenz/b,f/azepine-5-carboxamide

A suspension of 2.54 g (10 mmol) of 10-hydroxy-10,11-dihydro-5H-dibenz/b,f/azepine-5-carboxamide in 50 mL of 1,2-dichloroethane was treated with 1.23 g (15 mmol) of mixed acetic-formic anhydride and 1.36 g (20 mmol) of imidazole, the mixture was stirred at 25° C. for 3 hours and then it was poured into a stirred mixture of 100 mL 0.1M aqueous HCl and 50 g of ice. The organic layer was separated and extracted with a saturated solution of NaHCO₃, brine, and volatile components were removed by evaporation at reduced pressure. The remaining crude product was purified by chromatography on silica gel eluting first with methylene chloride and then with 1% methanol-methylene chloride mixture to give the desired product as white crystals of m.p. 202° to 203° C.

Example 2–3

By the application of the above described technique and related procedures known to those skilled in the art, and using appropriate anhydrides, 10-propionloxy-10,11-dihydro-5H-dibenz/b,f/azepine-5-carboxamide and 10-butyryloxy-10,11-dihydro-5H-dibenz/b,f/-azepine-5-carboxamide were prepared.

Example 4

(+)-10-acetoxy-10,11-dihydro-5H-dibenz/b,f/azepine-5-carboxamide

A solution of 9.42 g (0.12 mol) of acetylchloride in 100 mL of dichloromethane was added dropwise to a stirred and cooled (t<10° C.) suspension of 25.4 g (0.1 mol) of (−)-10-hydroxy-10,11-dihydro-5H-dibenz/b,f/azepine-5-carboxamide in 500 mL of dichloromethane and 11.9 g (0.15 mol) of pyridine. The reaction mixture was then stirred and boiled for two hours, then cooled to 5° C. and extracted subsequently with 500 mL of each 0.2M aqueous sulphuric acid, saturated aqueous sodium bicarbonate and brine. Organic phase was dried by sodium sulphate, filtered through a short pad of silica gel and volatile components of the filtrate were removed by evaporation under reduced pressure. The residue was crystallised from a mixture of dichloromethane and ethyl acetate to give the desired compound as white crystals (m.p. 186° to 187° C.),[α]$_D^{20}$=21.5° (c=1, pyridine).

Example 5–17

By the application of the above described technique and related procedures known to those skilled in the art, but using appropriate acid halogenides, following compounds were prepared:

10-benzoyloxy-10,11-dihydro-5H-dibenz/b,f/azepine-5-carboxamide 10-(4-methoxybenzoyloxy)-10,11-dihydro-5H-dibenz/b,f/azepine-5-carboxamide 10-(4-nitrobenzoyloxy)-10,11-dihydro-5H-dibenz/b,f/azepine-5-carboxamide 10-(4-chlorobenzoyloxy)-10,11-dihydro-5H-dibenz/b,f/azepine-5-carboxamide 10-ethoxycarbonyloxy-10,11-dihydro-5H-dibenz/b,f/azepine-5-carboxamide 10-(2-acetoxybenzoyloxy)-10,11-dihydro-5H-dibenz/b,f/azepine-5-carboxamide 10-pivaloyloxy-10,11-dihydro-5H-dibenz/b,f/azepine-5-carboxamide 10-stearoyloxy-10,11-dihydro-5H-dibenz/b,f/azepine-5-carboxamide 10-phenylacetoxy-10,11-dihydro-5H-dibenz/b,f/azepine-5-carboxamide 10-chloroacetoxy-10, 11-dihydro-5H-dibenz/b,f/azepine-5-carboxamide 10-bromoacetoxy-10,11-dihydro-5H-dibenz/b,f/azepine-5-carboxamide 10-(2-chloropropionyloxy)-10,11-dihydro-5H-dibenz/b,f/azepine-5-carboxamide

Example 18

10-nicotinoyloxy-10,11-dihydro-5H-dibenz/b,f/azepine-5-carboxamide

To a stirred suspension of 0.254 g (1 mmol) of 10-hydroxy-10,11-dihydro-5H-dibenz/b,f/azepine-5-carboxamide and 0.130 g (1 mmol) of nicotinic acid in 5 mL of tetrahydrofuran, 0.230 9 (1.1 mmol) of dicyclohexylcarbodiimide and 0.02 g (0.2 mmol) of 4-dimethylaminopyridine was added, and the mixture was stirred at 20° C. for six hours. Precipitated urea was removed by filtration, and the filtrate was evaporated under reduced pressure. The residue was chromatographed on silica gel with 0.5% methanol-dichloromethane mixture. Chromatographically homogeneous fractions were pooled, the solvents were distilled off under reduced pressure, and the residue was crystallised from acetonitrile to give the desired compound (m.p. 196° to 198° C.)

Example 19–23

By the application of the above described technique and related procedures known to those skilled in the art, but using appropriate acids, following compounds were prepared:

10-[(2-propyl)pentanoyloxy)]-10,11dihydro-5H-dibenz/b,f/azepine-5-carboxamide

10-[(2-ethyl)hexanoyloxy)]-10,11-dihydro-5H-dibenz/b,f/azepine-5-carboxamide 10-cyclohexanoyloxy-10,11-dihydro-5H-dibenz/b,f/azepine-5-carboxamide 10-(4-methoxyphenyl)acetoxy-10,11-dihydro-5H-dibenz/b,f/azepine-5-carboxamide 10-(4-nitrophenyl)acetoxy-10,11-dihydro-5H-dibenz/b,f/azepine-5-carboxamide

Example 24

10-(4-aminobutanoyloxy)-10,11-dihydro-5H-dibenz/b,f/azepine-5-carboxamide

A solution of isobutyl chloroformate (0.144 g, 1.05 mmol) in 2 mL of tetrahydrofuran was slowly added to a solution of 0.204 g (1 mmol) of N-tertbutoxycarbonyl-gamma-aminobutyric acid and 0.106 g (1.05 mmol) of triethylamine in 3 mL of tetrahydrofuran. The reaction mixture was stirred for 1 hour at –5° C., then filtered and the filtrate was added slowly to a suspension of 0.254 g (1 mmol) of 10-hydroxy-10,11-dihydro-5H-dibenz/b,f/azepine-5-carboxamide in 5 mL of tetrahydrofuran and 0.09 g (1.1 mmol) of pyridine. The reaction mixture was stirred for 4 hours at 25° C., then poured into 50 mL of a cold 5% solution of KHSO$_4$ and extracted with dichloromethane. The organic layer was extracted with a saturated aqueous solution of NaHCO$_3$ and brine, dried by sodium sulphate and volatile components were removed by distillation under reduced pressure. The residue was chromatographed on silica gel with 0.5% methanol in dichloromethane. Homogenous fractions were pooled and the solvent was evaporated in vacuo. The remaining protected derivative was dissolved in 10 mL of dichloromethane and 2 mL of trifluoroacetic acid. The reaction mixture was stirred for one hour at room temperature and then extracted with a cold saturated solution of NaHCO$_3$ and brine. The organic layer was dried by magnesium sulphate, evaporated to a small volume under reduced pressure, and then diluted with 5 mL of diethyl ether, and 2 mL of a 2% solution of HCl in diethyl ether were added. The precipitated crystals were collected by filtration and dried to give the hydrochloride of the desired compound. The salt was resuspended in 5 mL of aqueous solution of 2% sodium carbonate and extracted with 10 mL of dichloromethane. The organic solvent was dried by sodium sulphate and evaporated under reduced pressure to leave the desired product as an amorphous solid which decomposes without melting at approx. 120° C.

Example 25

Using similar procedure to that described in the preceeding example but employing the appropriate acid, 10-(2-amino-3-methylbutanoyloxy)-10,11-dihydro-5H-dibenz/b,f/azepine-5-carboxamide was prepared.

We claim:

1. A compound of general formula I, or stereoisomer thereof,

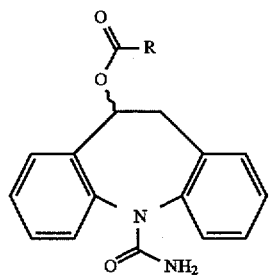

wherein: I

R is hydrogen, alkyl, halogenalkyl, aralkyl, cycloalkyl, cycloalkylalkyl, alkoxy, aryl or pyridyl; the term alkyl means carbon chain, straight or branched, containing from 1 to 18 carbon atoms; the term halogen represents fluorine, chlorine, bromine or iodine; the term cycloalkyl represents an alicyclic saturated group with 3 to 6 carbon atoms; and the term aryl represents unsubstituted phenyl group or phenyl substituted by alkoxy, halogen or nitro group.

2. A compound as defined in claim 1 which is:

(1) 10-acetoxy-10,11-dihydro-5H-dibenz/b,f/azepine-5-carboxamide (2) 10-benzoyloxy-10,11-dihydro-5H-dibenz/b,f/azepine-5-carboxamide (3) 10-(4-methoxybenzoyloxy)-10,11-dihydro-5H-dibenz/b,f/azepine-5-carboxamide (4) 10-(3-methoxybenzoyloxy)-10,11-dihydro-5H-dibenz/b,f/azepine-5-carboxamide (5) 10-(2-methoxybenzoyloxy)-10,11-dihydro-5H-dibenz/b,f/azepine-5-carboxamide (6) 10-(4-nitrobenzoyloxy)-10,11-dihydro-5H-dibenz/b,f/azepine-5-carboxamide (7) 10-(3-nitrobenzoyloxy)-10,11-dihydro-5H-dibenz/b,f/azepine-5-carboxamide (8) 10-(2-nitrobenzoyloxy)-10,11-dihydro-5H-dibenz/b,f/azepine-5-carboxamide (9) 10-(4-chlorobenzoyloxy)-10,11-dihydro-5H-dibenz/b,f/azepine-5-carboxamide

(10) 10-(3-chlorobenzoyloxy)-10,11-dihydro-5H-dibenz/b,f/azepine-5-carboxamide

(11) 10-(2-acetoxybenzoyloxy)-10,11-dihydro-5H-dibenz/b,f/azepine-5-carboxamide

(12) 10-propionyloxy-10,11-dihydro-5H-dibenz/b,f/azepine-5-carboxamide

(13) 10-butyryloxy-10,1-dihydro-5H-dibenz/b,f/azepine-5-carboxamide

(14) 10-pivaloyloxy-10,11-dihydro-5H-dibenz/b,f/azepine-5-carboxamide

(15) 10-[(2-propyl)pentanoyloxy]-10,11-dihydro-5H-dibenz/b,f/azepine-5-carboxamide

(16) 10-[(2-ethyl)hexanoyloxy]-10,11-dihydro-5H-dibenz/b,f/azepine-5-carboxamide

(17) 10-stearoyloxy-10,11-dihydro-5H-dibenz/b,f/azepine-5-carboxamide

(18) 10-cyclopentanoyloxy-10,11-dihydro-5H-dibenz/b,f/azepine-5-carboxamide

(19) 10-cyclohexanoyloxy-10,11-dihydro-5H-dibenz/b,f/azepine-5-carboxamide

(20) 10-phenylacetoxy-10,11-dihydro-5H-dibenz/b,f/azepine-5-carboxamide

(21) 10-(4-methoxyphenyl)acetoxy-10,11-dihydro-5H-dibenz/b,f/-azepine-5-carboxamide

(22) 10-(3-methoxyphenyl)acetoxy-10,11-dihydro-5H-dibenz/b,f/-azepine-5-carboxamide

(23) 10-(4nitrophenyl)acetoxy-10,11-dihydro-5H-dibenz/b,f/azepine-5-carboxamide

(24) 10-(3-nitrophenyl)acetoxy-10,11-dihydro-5H-dibenz/b,f/azepine-5carboxamide

(25) 10-nicotinoyloxy-10,11-dihydro-5H-dibenz/b,f/azepine-5-carboxamide

(26) 10-isonicotinoyloxy-10,11-dihydro-5H-dibenz/b,f/azepine-5-carboxamide

(27) 10-chloroacetoxy-10,11-dihydro-5H-dibenz/b,f/azepine-5-carboxamide

(28) 10-bromoacetoxy-10,11-dihydro-5H-dibenz/b,f/azepine-5-carboxamide

(29) 10-formyloxy-10,11-dihydro-5H-dibenz/b,f/azepine-5-carboxamide

(30) 10-ethoxycarbonyloxy-10,11-dihydro-5H-dibenz/b,f/azepine-5-carboxamide

(31) 10-(2-chloropropionyloxy)-10,11-dihydro-5H-dibenz/b,f/azepine-5-carboxamide.

3. A process for producing a compound having the general formula I of claim 1 comprising

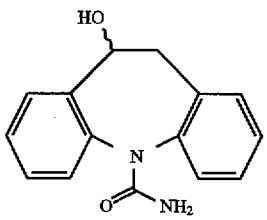

II with compounds of the general formula III

II wherein:

R is the same as defined above for general formula I;

A is hydrogen, halo or —O—CO—R group or —O—CO—OR' group, wherein R' is lower alkyl.

4. The process as defined in claim 3 wherein the reaction is conducted in the presence of at least one condensing agent or base.

5. In a method of treating a subject afflicted with epilepsy, trigeminal neuralgia, affective brain disorder or nervous function alteration in degenerative and post-ischemic disease by administering an effective amount of a pharmaceutical composition containing an active ingredient, the improvement which comprises employing a compound of claim 1 as said active ingredient.

6. The method of claim 5 in which the pharmaceutical composition comprises said compound of claim 1 in admixture with a pharmaceutically acceptable carrier.

7. In a method of treating a subject afflicted with epilepsy, trigeminal neuralgia, affective brain disorder or nervous function alteration in degenerative and post-ischemic disease by administering an effective amount of a pharmaceutical composition containing an active ingredient, the improvement which comprises employing a compound of claim 2 as said active ingredient.

8. The method of claim 7 in which the pharmaceutical composition comprises said compound of claim 1 in admixture with a pharmaceutically acceptable carrier.

9. A pharmaceutical composition comprising a compound according to claim 1 in admixture with a pharmaceutically acceptable carrier.

10. A pharmaceutical composition comprising a compound according to claim 2 in admixture with a pharmaceutically acceptable carrier.

* * * * *